United States Patent [19]

Coe et al.

[11] Patent Number: 5,059,208
[45] Date of Patent: Oct. 22, 1991

[54] ADJUSTABLE TRACHEOSTOMA VALVE

[75] Inventors: Frederick L. Coe; Edmund V. Seder, both of Santa Barbara, Calif.

[73] Assignee: Helix Medical, Inc., Santa Barbara, Calif.

[21] Appl. No.: 649,958

[22] Filed: Feb. 4, 1991

[51] Int. Cl.$^5$ ................................................ A61F 2/20
[52] U.S. Cl. ..................................... 623/9; 128/207.16
[58] Field of Search ....................... 623/9; 128/207.16; 137/521, 855, 856

[56] References Cited

U.S. PATENT DOCUMENTS

| | | |
|---|---|---|
| 3,747,127 | 7/1973 | Taub ......................................... 623/9 |
| 3,952,335 | 4/1976 | Sorce et al. ............................... 623/9 |
| 4,040,428 | 8/1977 | Clifford ..................................... 623/9 |

Primary Examiner—Randy Citrin Shay
Attorney, Agent, or Firm—Marvin E. Jacobs

[57] ABSTRACT

A patient adjustable valve to control the flow of air through an opening surgically created in the neck of the patient. Two concentrically rotatable tubular parts form the outer body and the inner annular sealing surface of the valve. A disk shaped diaphragm proximate the sealing surface allows the free passage of air to the trachea for lower breathing pressures but flaps closed for the higher pressures that precede speech. The normally curled diaphragm is pushed to a flatter, easier to close, position by a cam on the inside of the outer body when the body is rotated relative to the sealing surface.

14 Claims, 2 Drawing Sheets

ADJUSTABLE TRACHEOSTOMA VALVE

DESCRIPTION

1. Technical Field

This invention concerns the medical prostheses arts, especially combinations of air flow management valves used as a substitute for the larynx. In particular, a patient adjustable valve is described.

2. Background of the Invention

Normal human speech utilizes the flow of expired air from the lungs up through the trachea and the larynx to vibrate the vocal cords in the larynx. If disease or injury requires the removal of the larynx, it becomes necessary to provide alternative sound producing apparatus as a substitute for the vocal cords.

Since the larynx normally blocks the lungs from contamination by esophageal contents, the surgeon must block the passage between the trachea and the pharyngeal esophagus. Consequently at laryngectomy, the surgeon creates an opening, or stoma, at the base of the patients neck to which the trachea is permanently diverted. In one method of facilitating speech by the laryngectomee, the surgeon creates a new path for air to travel from the lungs and trachea to the pharyngeal esophagus. A voice prosthesis in the form of a cylindrically shaped, one-way valve is inserted into this tracheo-esophagal passageway. Furthermore, to permit such speech without manual occlusion of the stoma, a flange can be fastened over the tracheostoma and a valve inserted into the flange. This arrangement diverts the air flow from the trachea through the voice prosthesis.

It is known in the prior art to provide tracheostoma valves with a movable diaphragm biased to an open position. Normal breathing pressures are insufficient to move the diaphragm to a closed position. Hence, the patient may readily inhale and exhale past the diaphragm. Speech pressures, however, are initiated at somewhat higher levels. These higher pressures move the diaphragm to a closed position, blocking the free discharge of air to the atmosphere. The exhaled air can thus be diverted through the voice prostheses to the oral cavity where it produces sound that can be shaped into speech.

The present invention concerns the design of the tracheostoma valve itself. With different patients and changing exertion and respiration levels, no single diaphragm can have the correct mechanical characteristics to work ideally in all situations. In the past, it has been necessary for the doctor to select a compromise valve diaphragm that works best for an individual patient in an average state of exertion. This invention contemplates a new valve design that may be adjusted by the patient to work optimally even in changing circumstances.

Statement of the Prior Art

U.S. Pat. No. 3,952,335 to Sorce et al. discloses a tracheostoma valve in which a disk of flexible material serves as a diaphragm. The disk is operable to be moved by the elevated air flows of speech into a sealed position against a matching seat and close off the passageway from the trachea. This disk shaped diaphragm, which Sorce calls a flapper, is curled so as to normally assume a rest position away from the valve seat. Normal breathing generates in and out air flows that partly curl and uncurl the flapper a bit, but does not establish a seal. However, a higher pressure generated prior to initiation of speech pushes the flapper into a flat position against the valve seat, thus blocking the normal exhalation of air into the atmosphere. Instead, the exhaled air is diverted out the side of the valve through a different conduit to the oral pharynx.

The shortcomings of this approach are well explained by Sorce. Since respiratory characteristics vary widely from patient to patient, it is impractical to specify the degree of flexibility, or spring rate, of the flapper. Instead, the flapper must be customized to each patient. At the present time, the doctor usually chooses from among three thicknesses of flapper for the dynamic characteristics that are most comfortable for the patient. But even if one of these choices works acceptably in one circumstance, it may well work poorly in another such as when the patient is more active and increases his breathing rate. It is clearly desirable to be able to make the valve adjustable to changing circumstances. The present invention achieves this end, providing means by which the patient may effect a wide range of adjustment himself as conditions require.

SUMMARY OF THE INVENTION

Briefly, our invention contemplates a tracheostoma valve that uses a curled flexible disk diaphragm that moves into sealing engagement with a matching seat in response to higher air flow rates initiated prior to speech as in the prior art. However, the valve is constructed from two concentrically rotating parts. One part, the seat, carries the diaphragm and the matching sealing seat. The other part, the body, carries an inwardly projecting cam that contacts the diaphragm near its center on the concave side. When the body is rotated relative to the seat, the cam pushes the curled diaphragm to a flatter position. The resulting smaller air passage forces an increase in the air velocity through the passage. This, in turn, generates a low pressure area on the back side of the curled diaphragm causing it to close more readily. Consequently, even though the diaphragm has a constant thickness and spring rate, it can be adjusted to close more or less easily by simply rotating the two valve parts relative to each other. Hence, the user is able to easily adjust the dynamics of the valve at any time for the most comfortable operation.

The details of the design along with additional benefits and advantages are explained hereinafter.

DETAILED DESCRIPTION OF THE INVENTION

Figure 1:
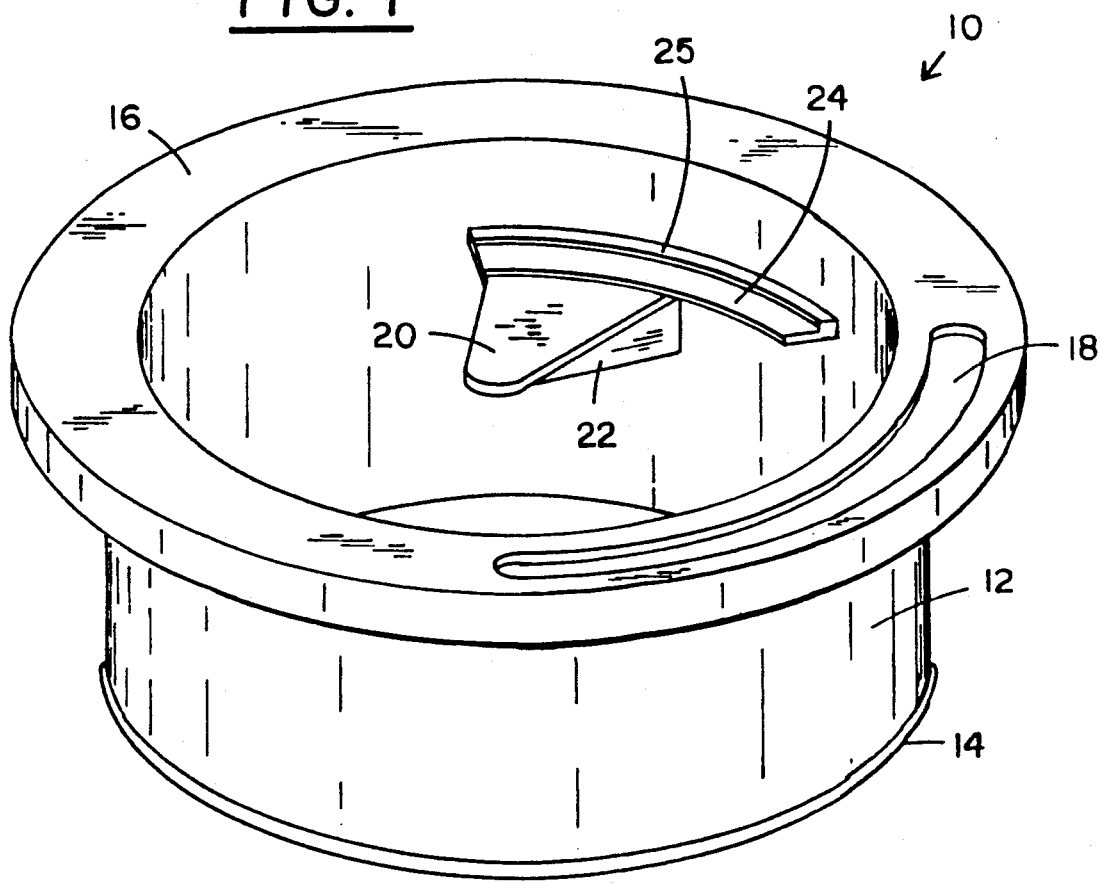
FIG. 1 is a perspective view of the body of the tracheostoma valve showing the inwardly projecting cam therein.

FIG. 1 shows the body 10 of the tracheostoma valve. A cylindrical tube portion 12 is sized to fit securely into a base flange that is taped or glued to the patients neck over the tracheostoma. A small raised ridge 14 may be formed on tube 12 to lock the tube into the base flange. The base flange is not shown in the drawings for the sake of clarity.

The valve parts may be molded from a suitable plastic such as polypropylene. Body 10 includes a bearing flange 16 with a recessed channel 18 extending about a quarter of the way around the circumference of the bearing face of bearing flange 16. A cam 20 projects inwardly from tube 12 at an angle to a normal radius line. Cam 20 is additionally buttressed by a member 22 underneath and a shelf 24 above.

Figure 2:
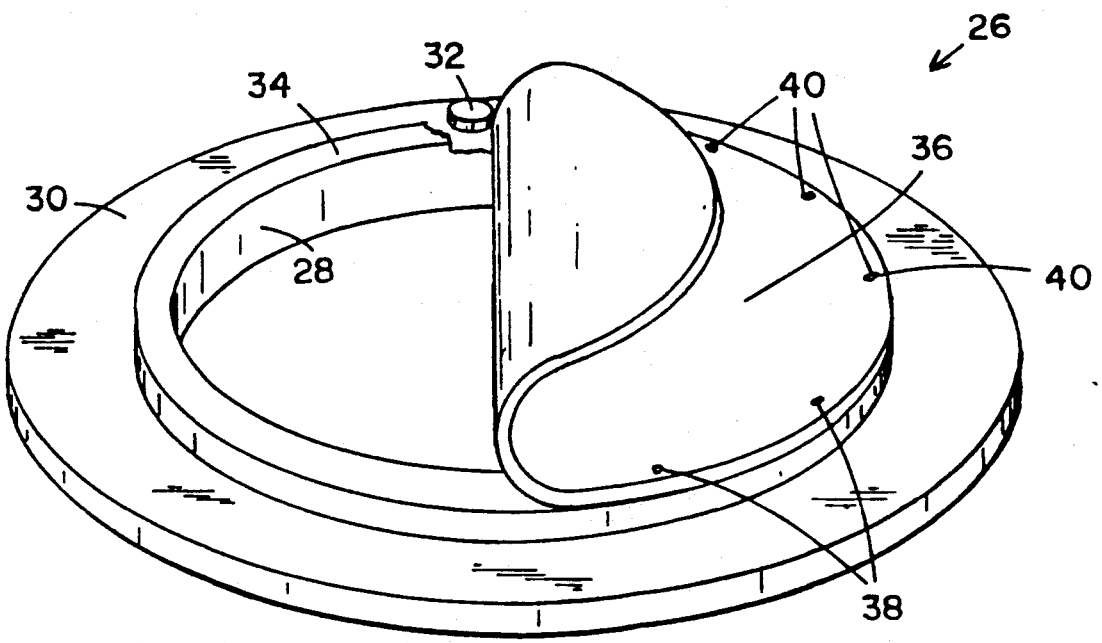
FIG. 2 is a perspective view of the valve seat with the flexible diaphragm mounted thereon.

FIG. 2 shows the valve seat 26. Seat 26 has a short tubular portion 28 sized to fit smoothly inside the top of tube 12 in FIG. 1. When so fitted, a bearing flange surface 30 comes into facing contact with the bearing face of bearing flange 16. A limit pin 32 is formed on flange surface 30 that enters into and engages recessed channel 18 on the body 10. Tube 28 is partly cut away in FIG. 2 to better show pin 32.

A generally flat sealing surface 34 is provided at the end of tube 28 to make sealing contact with a flexible disk shaped diaphragm 36. Diaphragm 36 is mounted on sealing surface 34 by means of a plurality of pegs 38 and 40 that extend up from sealing surface 34 through holes in the edge of diaphragm 36. In this way, a new diaphragm may be inserted into the valve quite easily by pulling the old diaphragm off the pegs and pushing on the new diaphragm and then snapping the body 10 and seat 26 back together.

Diaphragm 36 is formed from a soft flexible material such as silicone elastomer and incorporates a curled shape so as to normally assume the position shown in FIG. 2. The assembled valve has seat 26 turned over from the orientation of FIG. 2 and snapped into body 10 with the curled diaphragm around cam 20 and the pegged edge of the diaphragm resting against the top of shelf 24. Shelf 24 traps the diaphragm on the pegs during use as is more easily seen in FIG. 3.

Figure 3:
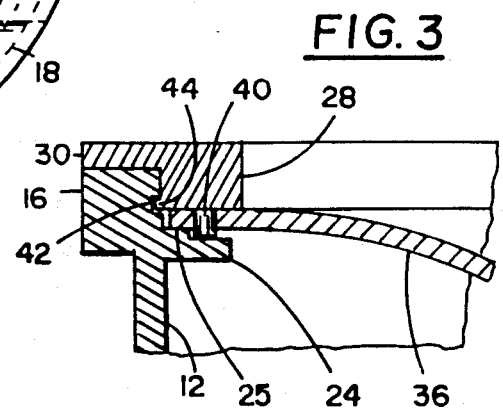
FIG. 3 is a fragmentary sectional detail showing how the seat and body snap together into a concentrically rotating relationship.

FIG. 3 shows a fragmentary sectional view of the assembled valve with bearing flange 30 against bearing flange 16 and tube 28 inside tube 12. It may be seen that diaphragm 36, mounted on peg 40, is trapped on the pegs by shelf 24. Additionally, shelf 24 includes a slightly raised step portion 25 that fits behind the pegs, near the inside wall of tube 12, so as to keep diaphragm 36 in good sealing contact with surface 34. FIG. 3 also shows structure not included in the other Figures, namely, a circumferential groove 42 on the inside of tube 12 that accepts and retains a circumferential ridge 44 on the outside of tube 28. Groove 42 and ridge 44 cooperate to keep body 10 and seat 26 snapped together during their relative rotation. The operation of the cam 20 is more easily seen in FIGS. 4 and 5.

Figure 4:
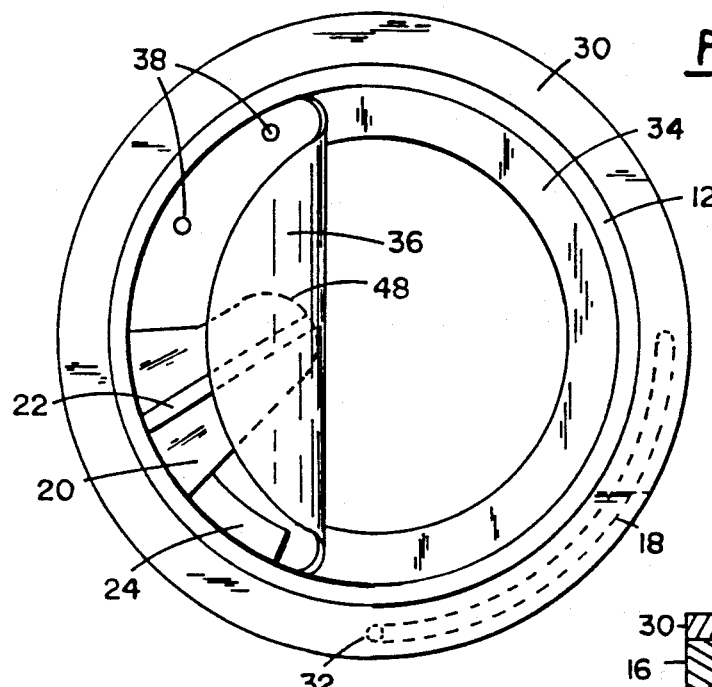
FIG. 4 is an end view of the assembled valve, as seen from the trachea side of the valve, showing the diaphragm in the fully open position.
Figure 5:
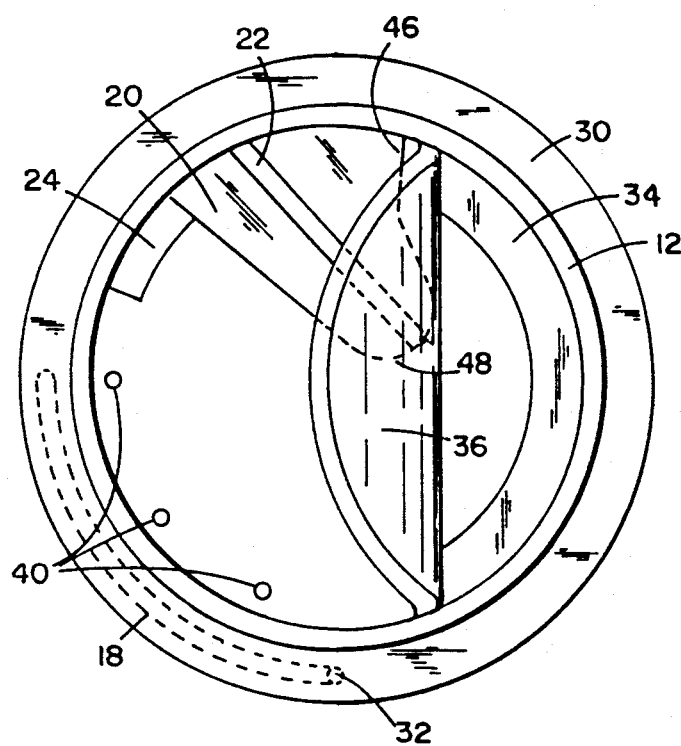
FIG. 5 is identical to FIG. 4 but with the cam rotated so as to uncurl the diaphragm and make the passageway smaller.

In FIG. 4, body 10 and cam 20 are at the maximum counterclockwise rotational position relative to seat 26 and diaphragm 36 with pin 32 against one end of arcuate recess 18. In this position, cam 20 contacts the concave side of the curled diaphragm near the center in such a way that diaphragm 36 covers less than half of the air passage through tube 12. It should be noticed that, although pegs 38 are uncovered in this position, pegs 40 are still covered by shelf 24 so that diaphragm 36 remains well secured. Rotation of the body 10 clockwise moves cam 20 progressively farther to the right so as to uncurl and flatten diaphragm 36 gradually making it easier to close by air pressure from the lungs. After about ninety degrees of rotation, the configuration of FIG. 5 is reached. In FIG. 5, pin 32 reaches the other end of recess 18 limiting further rotation so that the valve does not close entirely. At this position, pegs 40 become uncovered but pegs 38 are now covered by shelf 24. Thus, some pegs are always covered and the diaphragm is always trapped securely in place.

Cam 20 is angled and also relieved at 46 so as to avoid excessive wear at the edge of the delicate silicone diaphragm 36. The rounded tip 48 also avoids wear. The angle of cam 20 is chosen to keep the tip 48 generally near the center of the curled diaphragm so as to uncurl it evenly. Although a quarter turn of relative rotation has been found to provide a good range of air pressure response, more or less relative rotation may be used simply by varying the length of recess 18. Other variations are apparent without departing from the scope and spirit of the appended claims including modified cam shapes, shelf shapes, and diaphragm shapes. Hence, limitation in accordance only with the claims is intended.

We claim:

1. An adjustable valve adapted to control the flow of air through a tracheostoma comprising in combination:
   a valve seat having a sealing surface thereon and an opening therethrough;
   a flexible diaphragm mounted proximate to said opening and shaped to engage said sealing surface and close said opening in response to airflow through said opening at a predetermined rate, said diaphragm normally assuming a position removed from said sealing surface for air flow less than said predetermined rate; and
   a valve body movably connected to said seat so as to be movable between first and second positions relative to said seat, including a cam means on said body for engaging to engage said diaphragm and varying the distance between said diaphragm and said sealing surface in accordance with the movement of said body relative to said seat and between said first and second positions.

2. The valve of claim 1 in which said body is generally cylindrical in shape and said seat is also generally cylindrically shaped and sized to rotate concentrically within said body between said first and second positions.

3. The valve of claim 2 in which said cam comprises an inwardly projecting member extending from the inside of said cylindrical body so as to engage said diaphragm.

4. The valve of claim 3 in which said opening in said seat is approximately circular and said sealing surface is disposed about the periphery of said opening and said diaphragm comprises a generally disk shaped membrane mounted on pegs about part of said sealing surface.

5. The valve of claim 4 in which said diaphragm is normally curled away from said sealing surface so as to have a concave side, said cam contacting the diaphragm on said concave side.

6. The valve of claim 5 including a retaining shelf extending inward from a part of the inside surface of said cylindrical body so as to hold said diaphragm on said pegs.

7. The valve of claim 6 including a pin on said seat extending into an arcuate recess in a portion of the circumference of said body so as to limit the amount of relative rotation of the seat and the body.

8. An adjustable tracheostoma valve comprising in combination:
- a tubular body;
- an annular sealing surface situated for concentric rotation within said body;
- a flexible diaphragm mounted about part of said sealing surface so as to be proximate to but not in contact with said sealing surface; and
- projecting means extending inward from the inside surface of said tubular body, said projecting means operable to move said diaphragm closer to said sealing surface when said body is rotated relative to said annular sealing surface.

9. The valve of claim 8 including concentric rotation limiting means between said body and said sealing surface.

10. The valve of claim 8 including pegs on said part of said sealing surface that pass through holes in said diaphragm so as to hold said diaphragm in place.

11. The valve of claim 10 including a shelf member on the inside surface of said tubular body located to hold said diaphragm on said pegs.

12. The valve of claim 11 including a raised step on said shelf member sized to fit past said pegs and urge said flexible diaphragm against said sealing surface.

13. The valve of claim 12 including concentric rotation limiting means between said body and said sealing surface.

14. The valve of claim 11 including concentric rotation limiting means between said body and said sealing surface.

* * * * *

UNITED STATES PATENT AND TRADEMARK OFFICE
CERTIFICATE OF CORRECTION

PATENT NO. : 5,059,208
DATED : October 22, 1991
INVENTOR(S) : Federick L. Coe; Edmund V. Seder; Eric D. Blom It is certified that error appears in the above-identified patent and that said Letters Patent is hereby corrected as shown below:

Title page, Column 1, in [75] Line 2, after "Calif." add --and Eric D. Blom of Indianapolis, Indiana--

Signed and Sealed this

Seventeenth Day of August, 1993

Attest:

BRUCE LEHMAN

Attesting Officer     Commissioner of Patents and Trademarks